(12) United States Patent  
Maschke et al.

(10) Patent No.: US 7,933,641 B2  
(45) Date of Patent: Apr. 26, 2011

(54) MEDICAL EXAMINATION AND/OR TREATMENT APPARATUS WITH AN ELECTROMAGNET FOR NAVIGATING A MEDICAL INSTRUMENT AND AN X-RAY DEVICE FOR VISUAL INSPECTION DURING THE NAVIGATION

(75) Inventors: Michael Maschke, Lonnerstadt (DE); Klaus Klingenbeck-Regn, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 888 days.

(21) Appl. No.: 11/901,682

(22) Filed: Sep. 18, 2007

(65) Prior Publication Data

US 2008/0103388 A1 May 1, 2008

(30) Foreign Application Priority Data

Sep. 25, 2006 (DE) .......................... 10 2006 045 176

(51) Int. Cl.  
*A61B 5/05* (2006.01)

(52) U.S. Cl. ....................................... 600/427; 600/424

(58) Field of Classification Search .......... 600/425–429; 606/130; 378/4, 11–17, 21, 62, 63, 68; 250/370.08, 250/370.09; 901/2, 16  
See application file for complete search history.

(56) References Cited

U.S. PATENT DOCUMENTS

| | | | |
|---|---|---|---|
| 5,406,946 A | 4/1995 | Imran | |
| 5,540,959 A | 7/1996 | Wang | |
| 5,713,357 A * | 2/1998 | Meulenbrugge et al. | 600/411 |
| 6,241,671 B1 | 6/2001 | Ritter et al. | |
| 6,459,924 B1 * | 10/2002 | Creighton et al. | 600/427 |
| 6,713,671 B1 | 3/2004 | Wang et al. | |
| 2002/0100486 A1 | 8/2002 | Creighton, IV et al. | |
| 2003/0137380 A1 | 7/2003 | Creighton, IV | |

FOREIGN PATENT DOCUMENTS

| | | |
|---|---|---|
| DE | 4436828 C1 | 3/1996 |
| DE | 10119228 A1 | 5/2002 |
| DE | 10340925 B3 | 6/2005 |
| DE | 10341092 A1 | 7/2005 |
| DE | 102004057308 A1 | 7/2006 |
| DE | 10 2005 010 489 A1 | 9/2006 |
| EP | 1 547 540 A1 | 6/2005 |

OTHER PUBLICATIONS

Fahrig et al. A Truly Hybrid Interventional MR/X-Ray System: Feasibility Demonstration. Journal of Magnetic Resonance Imaging. 13:294-300. 2001.*  
Ganguly et al (Truly Hybrid X-Ray/MR Imaging: Toward a Streamlined Clinical System. Academic Radiology. 12(9). Abstract. 2005.*

(Continued)

*Primary Examiner* — Brian Casler  
*Assistant Examiner* — Parikha S Mehta

(57) ABSTRACT

There is described a medical examination and/or treatment apparatus with an electromagnet for generating a magnetic field for navigating a medical instrument and an x-ray device having an x-ray source and an x-ray detector attached to a bracket for visual control during the navigation, with the x-ray source and the x-ray detector being arranged on the electromagnet embodied as a hollow cylinder, on the front ends of which are located two ring coils which are arranged in parallel, between which a number of saddle coils arranged in the peripheral direction are arranged, with the hollow cylinder being arranged on a bracket which can be moved about a number of axes.

19 Claims, 5 Drawing Sheets

OTHER PUBLICATIONS

Biophan Technologies Inc., "MRI Shielding For Medical Devices", Retrieved from Internet Jul. 11, 2005: http://www.biophan.com/shielding.php, Pages pp. 1-5, 1 of 1.

Siemens AG, Medical Solutions/Angiography, Fluoroscopic and Radiographic Systems; "AXIOM Artis dFC/dBC Magnetic Navigation, Single/biplane C-arm system with dynamic flat detector for magnetic assisted intervention with the Stereotaxis NIOBE® system"; © Jun. 2005 Siemens AG, pp. 1-20, Order No. A91601-M1400-G949-1-7600, Printed in Germany, AX CRM NA 06053.

* cited by examiner

MEDICAL EXAMINATION AND/OR TREATMENT APPARATUS WITH AN ELECTROMAGNET FOR NAVIGATING A MEDICAL INSTRUMENT AND AN X-RAY DEVICE FOR VISUAL INSPECTION DURING THE NAVIGATION

CROSS REFERENCE TO RELATED APPLICATIONS

This application claims priority of German Patent Office application No. 10 2006 045 176.7 DE filed Sep. 25, 2006, which is incorporated by reference herein in its entirety.

FIELD OF INVENTION

The invention relates to a medical examination and/or treatment apparatus, comprising an electromagnet for generating a magnetic field in order to navigate a medical instrument and an x-ray device having an x-ray source attached to a bracket and an x-ray detector for visual inspection during navigation.

BACKGROUND OF INVENTION

Minimally-invasive interventions are performed in order to treat diseases of the heart or other hollow organs, by inserting a medical instrument, for instance a catheter or an ablation catheter, into the organ to be treated. In this way, an ablation catheter can be inserted into the atrium by way of intravenous access, where it thermally cuts interfering nerve conduction paths in two by means of high-frequency energy. The prerequisite for this therapy is however that the ablation catheter is moved to precisely the right point and that the intervention is monitored using an imaging method.

An apparatus for navigating a medical instrument is known from US 2003/0137380 A1. Two special rotatable and pivotable permanent magnets are used there on the left and right side of the patient bed at the level of the heart region, said permanent magnets lying opposite one another. The intervention is monitored here using an imaging apparatus, like an x-ray device for instance. An x-ray source and an x-ray detector are arranged here opposite one another and generate fluoroscopy images of the patient during the magnetic navigation of a guide wire or catheter. With the apparatus known from US 2003/0137380 A1, the two magnets for generating the magnetic field are located on the right and left of the patient, who is lying on a patient support table. This apparatus is disadvantageous in that patient accessibility is poor, and at the same time the heavy and bulky permanent magnets result in high installation costs.

SUMMARY OF INVENTION

An object underlying the invention is thus to specify a medical examination and/or treatment apparatus, with which patient accessibility is improved.

In order to solve this problem, provision is made in accordance with the invention with a medical examination and/or treatment apparatus of the type mentioned at the start for the x-ray source and x-ray detector to be arranged on the electromagnet embodied as a hollow cylinder, on the front ends of which are located two ring coils which are parallel to one another, and between which a number of saddle coils arranged in the peripheral direction are arranged, with the hollow cylinder being arranged on a bracket which can be moved about a number of axes.

The apparatus according to the invention is advantageous in that the ring coils and saddle coils are located comparatively close to the patient, who can be accommodated in the hollow cylinder, thereby ensuring that a magnetic field with a minimal field strength is sufficient for the navigation of the medical instrument. Since there is no need for bulky and heavy permanent magnets, good patient accessibility can be ensured. A further advantage can consist in the x-ray source and the x-ray detector being arranged on the electromagnet which is embodied as a hollow cylinder, with said electromagnet being realized such that the x-rays are not disadvantageously influenced by the hollow cylinder. The saddle coils preferably comprise corresponding openings, which can be penetrated by the x-rays. With the medical examination and/or treatment apparatus according to the invention, as the hollow cylinder is arranged on a bracket which can be moved about a number of axes, the hollow cylinder and thus the magnetic-field-generating facility can be positioned in a particularly flexible and precise manner so that all organs of a patient, on which or in which an examination or intervention is to be carried out, can be reached.

According to an advantageous development of the invention, provision can be made for the bracket to comprise a number of mounting arm segments which are connected to one another in a jointed manner. These mounting arm segments can be used in a manner similar to that of a robot arm and enable the hollow cylinder to be moved about a number of axes in practically any manner.

With the medical examination and/or treatment apparatus according to the invention, provision can be made for the x-ray source and x-ray detector to be moveable along the periphery of the hollow cylinder by means of a drive. The relative position of the x-ray system consisting of the x-ray source and the x-ray detector in respect of the hollow cylinder can be changed in this manner, so that optimum fields of view can be set for each examination. The hollow cylinder and if necessary the x-ray detector can be moved by means of a control facility. It is also possible for more than one x-ray source and more than one x-ray detector to be present.

To prevent the hollow cylinder from overheating, said hollow cylinder can feature a cooling apparatus. The required current strength can also be reduced by cooling. Thermal interferences of the x-ray source or x-ray detector can herewith also be avoided, which arise in the region of the coils.

Provision can also be made for a control facility for controlling the electromagnet and for navigating the medical instrument by influencing the current strength and/or the current direction in the ring coil and/or the saddle coil. The size and direction of the magnetic field can be influenced in this manner, in order to navigate the medical instrument, a catheter for instance, to the desired location in the body of a patient.

The electromagnet of the medical examination and/or treatment apparatus in accordance with the invention can be embodied such that the saddle coils can be rotated relative to the ring coils about the longitudinal axis of the hollow cylinder in order to generate the magnetic field in the desired operating volume. This is particularly preferred, such that the hollow cylinder comprises four saddle coils, which are preferably arranged in the peripheral direction.

With the medical examination and/or treatment apparatus according to the invention, provision can be made for it to comprise a moveable patient support table, which can be adjusted by means of a or the control facility. The adjustment is preferably effected synchronously with the adjustment of the hollow cylinder or is attuned thereto.

In accordance with a development of the invention, provision can be made for the x-ray detector to comprise a coating made of preferably conductive nanoparticles in order to shield against magnetic fields.

The current clock for generating the electromagnetic field can similarly be synchronized with the readout of the x-ray detector in order to generate the electromagnetic field, and in order to avoid image artifacts.

BRIEF DESCRIPTION OF THE DRAWINGS

Further advantages and details of the invention are described in more detail on the basis of exemplary embodiments with reference to the figures, in which.

DETAILED DESCRIPTION OF INVENTION

Figure 1:
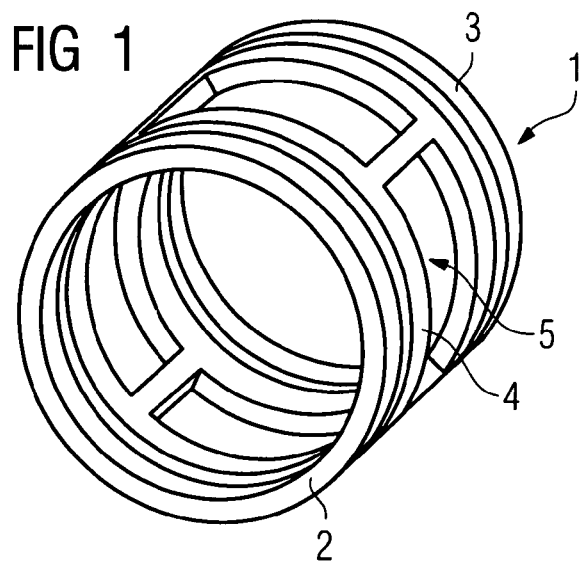
FIG. 1 shows a schematic representation of a hollow cylinder with ring and saddle coils according to a first exemplary embodiment of the apparatus according to the invention.

FIG. 1 shows an electromagnet embodied as a hollow cylinder 1, which comprises ring coils 2, 3, which are arranged on both ends of the hollow cylinder 1 and between which are located saddle coils 4. In the exemplary embodiment illustrated, the hollow cylinder 1 comprises four saddle coils 4 which are distributed over the periphery, said saddle coils bordering one another in the peripheral direction. The saddle coils 4 consist in each instance of radial and axial coil segments, which each delimit a coil opening 5. By controlling the coil currents, a magnetic field is generated in the interior of the hollow cylinder 1 in an operating volume, with the aid of which a magnetic instrument can be navigated.

Figure 2:
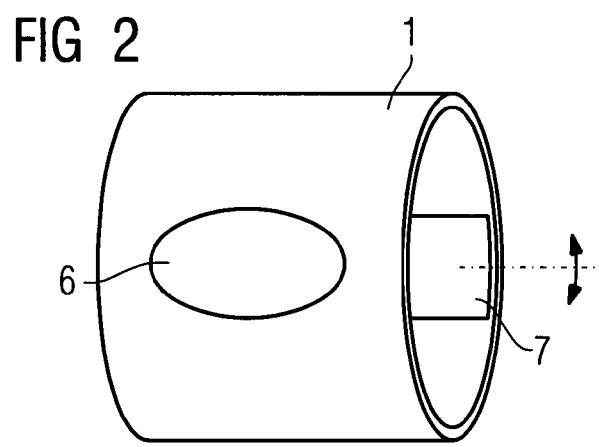
FIG. 2 shows a schematic representation of the hollow cylinder with the x-ray source and x-ray detector.
Figure 3:
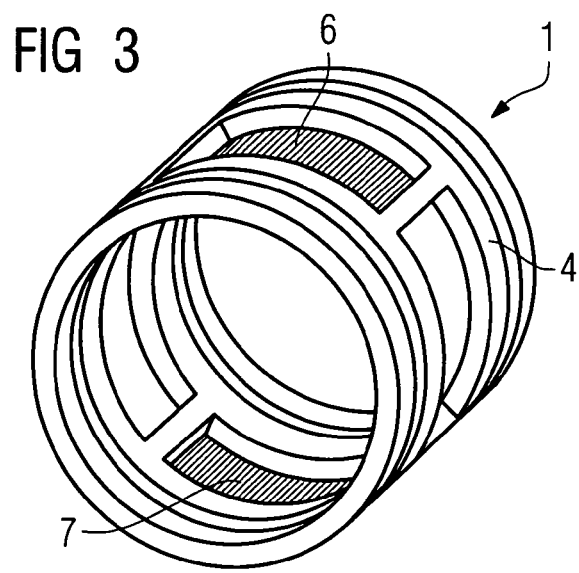
FIG. 3 shows a schematic representation of a hollow cylinder with a rotatable x-ray source and x-ray detector as claimed in a second exemplary embodiment.
Figure 4:
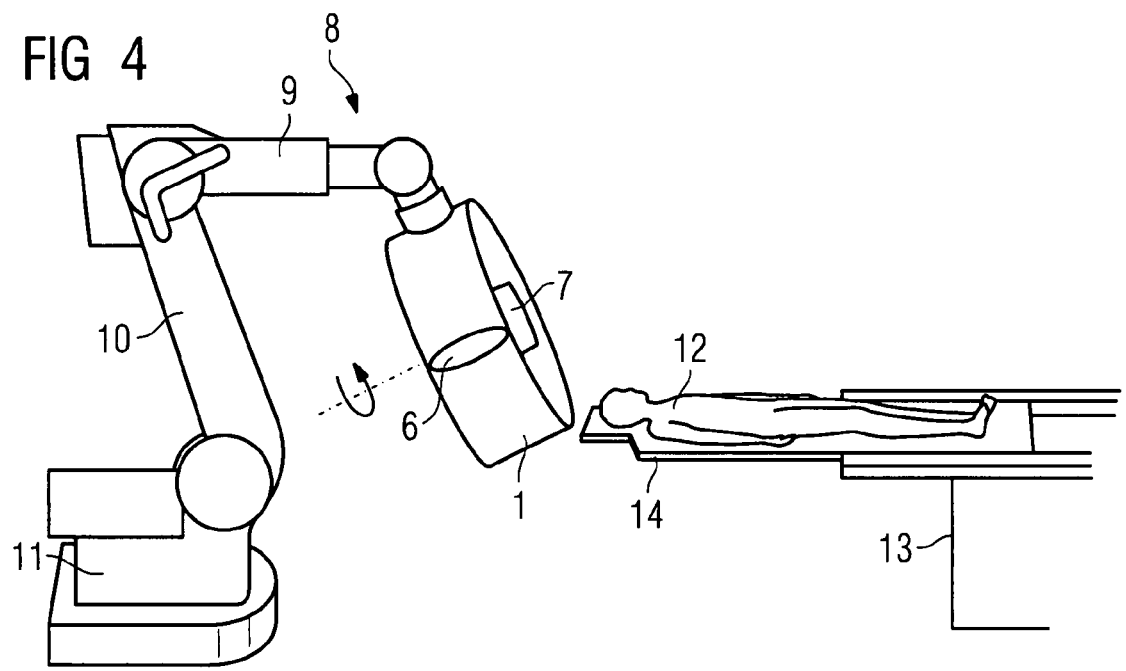
FIG. 4 shows a schematic representation of an examination and/or treatment apparatus in a side view.
Figure 5:
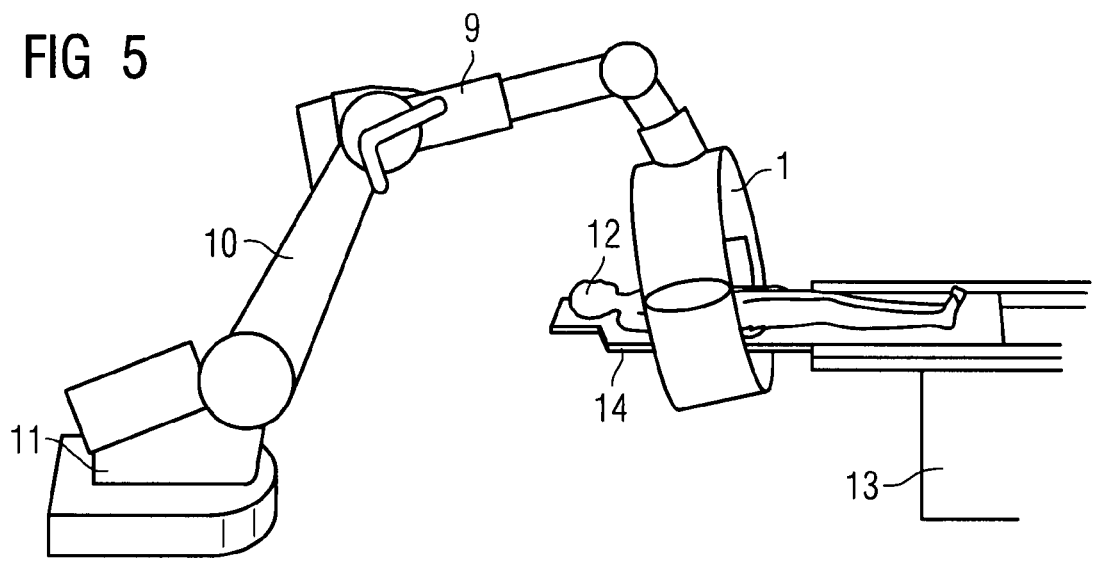
FIG. 5 shows a schematic representation of a further side view of the apparatus in FIG. 4.
Figure 6:
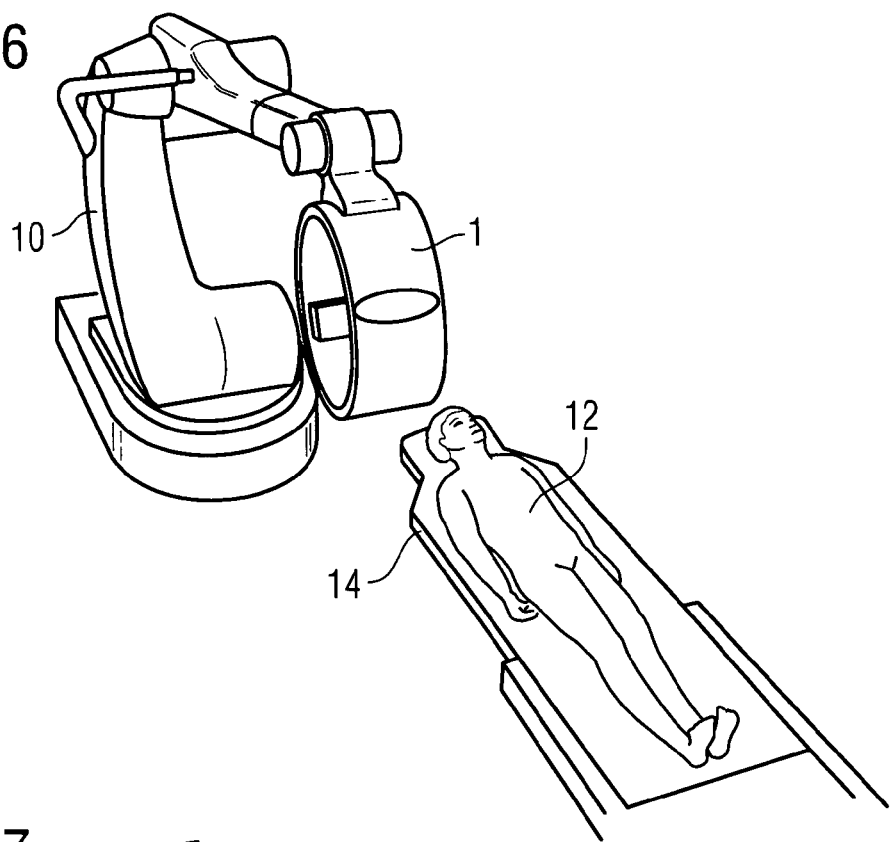
FIG. 6 shows a schematic representation of a perspective view of the apparatus in FIG. 4.
Figure 7:
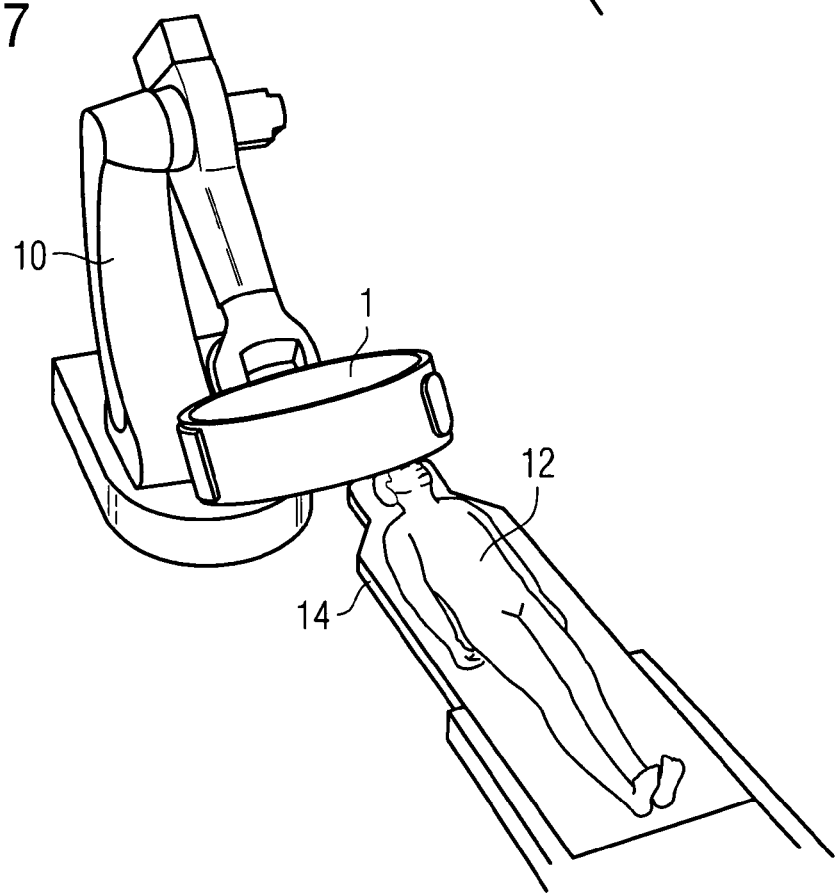
FIG. 7 shows a schematic representation of a further perspective view of the apparatus in FIG. 4.

FIGS. 2 and 3 show hollow cylinders, which are provided with an x-ray source 6 and an x-ray detector 7. In the exemplary embodiment in FIG. 2, the x-ray source 6 and x-ray detector 7 are attached in a fixed position, with the attachment being carried out such that the x-ray source 6 and x-ray detector 7 are not interrupted by the ring coils 2, 3 and the saddle coils 4. The x-ray source 6 and x-ray detector 7 are automatically moved when the hollow cylinder 1 is moved or rotated, with the direction of rotation being specified by the arrow in FIG. 2.

FIG. 3 shows a second exemplary embodiment of a hollow cylinder, with the x-ray source 6 and x-ray detector 7 being attached to the saddle coils 4 such that if the saddle coils 4 are rotated, they move synchronously thereto.

The apparatus according to the invention is described in more detail below with reference to the FIGS. 4 to 7. FIGS. 4 to 7 show different views of an exemplary embodiment of the examination and/or treatment apparatus. The apparatus 8 shown in FIG. 4 comprises the hollow cylinder 1 with x-ray source 6 and x-ray detector 7. The hollow cylinder 1 is attached to a bracket, which consists of a number of mounting arm segments 9, 10 which are connected to one another in a jointed manner and a base body 11 which is mounted to the base. During an examination or an intervention, a patient 12 is located on a patient support table 13, the table plate 14 of which can be moved in the direction of the longitudinal axis of the patient. The height of the table plate 14 can likewise be changed. The table plate 14 can additionally be rotated about the longitudinal axis of the patient 12 as an axis of rotation.

In order to perform an examination or intervention, the apparatus 8 is used in a manner similar to that of a robot arm, by positioning the hollow cylinder 1, which comprises the coils for generating the magnetic field as well as the x-ray source 6 and the x-ray detector 7, such that the organ to be examined is located in the isocenter. In addition, the mounting arm segments 9, 10 which are mounted in a jointed manner are correspondingly controlled and moved. The size of the hollow cylinder 1 is selected here such that it can be moved about the table plate 14 of the patient support table 13 and thus about the patient 12, which can be best seen in FIG. 5. The hollow cylinder 1 is rotated accordingly in the peripheral direction, until the x-ray source 6 and x-ray detector 7 are optimally positioned. With other exemplary embodiments, an ellipsoid cavity can be used instead of a hollow cylinder, so that the x-ray source and x-ray detector can rotate about the patient on an elliptical path. With the x-ray apparatus attached to the hollow cylinder 1, said x-ray apparatus consisting of the x-ray source 6 and the x-ray detector 7, 2D projection recordings can be created and registered. Correspondingly controlling the mounting arm segments 9, 10 of the apparatus 8 allows the hollow cylinder 1 to be moved and/or rotated, as a result of which the desired control of the medical object, a catheter for instance, is effected by virtue of the magnetic field generated.

Two different embodiments of the hollow cylinder are essentially possible, the x-ray source 6 and x-ray detector 7 can either be moved and rotated synchronously with the ring coils 2, 3 of the hollow cylinder 1, in this case the x-ray source 6 and x-ray detector 7 are fastened to the hollow cylinder 1 or the ring coils 2. Alternatively the x-ray source 6 and x-ray detector 7 can be fastened to the saddle coils 4 so that they can be rotated relative to the ring coils 2, 3 in the peripheral direction.

In the exemplary embodiment illustrated, the x-ray detector 7 is an aSi detector, which features low sensitivity to magnetic fields. An optional thin film layer made of conductive nanoparticles, which can consist for instance of silicon dioxide, aluminum dioxide, silicon nitrate or carbon, is located on the x-ray detector 7. A magnetic shielding can be achieved using these conductive nanoparticles.

While the intervention is being performed, the x-ray source 6 and x-ray detector 7 move about an angular range of approximately 180° and record a rapid sequence of projection images. 3D images are reconstructed from these 2D projection recordings, with it being possible for methods for 3D soft part reconstruction to be used. It is also possible for the reconstruction to relate only to a subset of the recorded data, for instance a sub region can only comprise an angular range of 90°.

An ECG signal can optionally be detected during the examination or intervention, so that in the subsequent processing only image recordings are used which were recorded during specific heart phases. This prevents artifacts as a result of the beating heart or other influences. To improve the evaluation and visualization of the projection recordings, a contrast agent can be administered beforehand to the patient.

Figure 8:
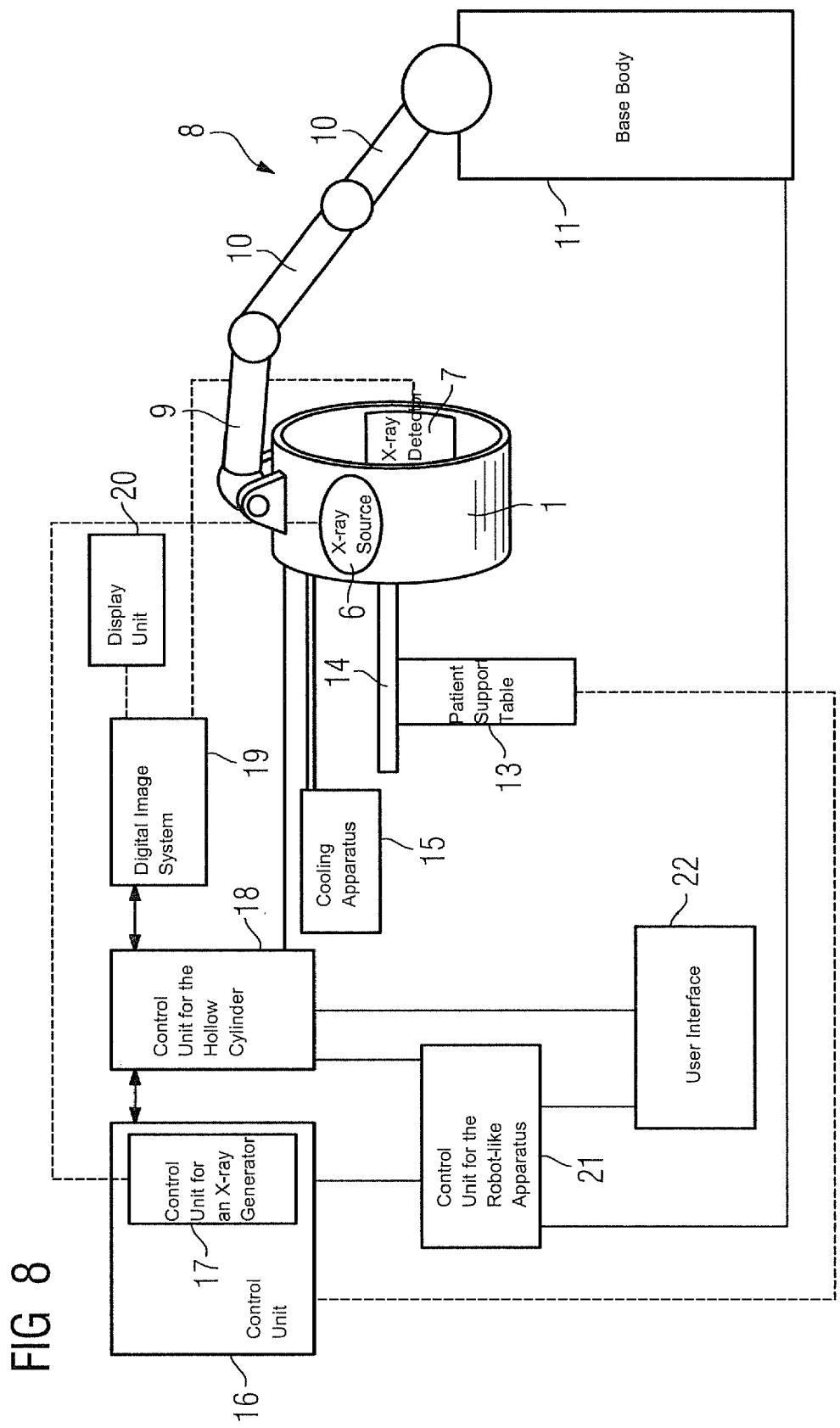
FIG. 8 shows a schematic representation of the individual components of the examination and/or treatment apparatus according to the invention.

FIG. 8 shows a schematic representation of the individual components of the examination and treatment apparatus.

In addition to the components already mentioned, the apparatus comprises a cooling apparatus 15, which is connected to the hollow cylinder 1 and prevents the coils from overheating during operation. At the same time, the required current strength is reduced by the cooling process.

A control unit 16 of the x-ray system is also shown schematically in FIG. 8, said control unit 16 having a control unit 17 for an x-ray generator. The control unit 16 is coupled to a control unit 18 for the hollow cylinder 1, which comprises the ring coils 2, 3 and the saddle coils 4 in order to generate the magnetic field. The x-ray detector 7 is connected to a digital image system 19 which is illustrated schematically, said image system 19 comprising a soft tissue processor. The digital image system 19 and the control unit 18 can exchange data with one another. A display unit 20 for displaying the processed 2D or 3D image data is connected to the digital image system 19.

A separate control unit 21 for the robot-like apparatus 8 is connected to a user interface 22 for the x-ray system and the system for the magnetic navigation.

The required electromagnetic fields are generated by way of clocked power supply units. This current clocking normally results in image distortions in the digital x-ray recording chain, consisting of a detector, preprocessing and image system and only allows either navigation or image generation. To avoid these problems, provision is made to synchronize the current clocking for generating the electromagnetic navigation field with the image readout clocking of the x-ray recording chain so that image artifacts generated by the current clocking are avoided. To this end, only one image on the x-ray detector is then generated and read out if none or only a small amount of current is flowing in order to generate the electromagnetic navigation field.

Figure 9:
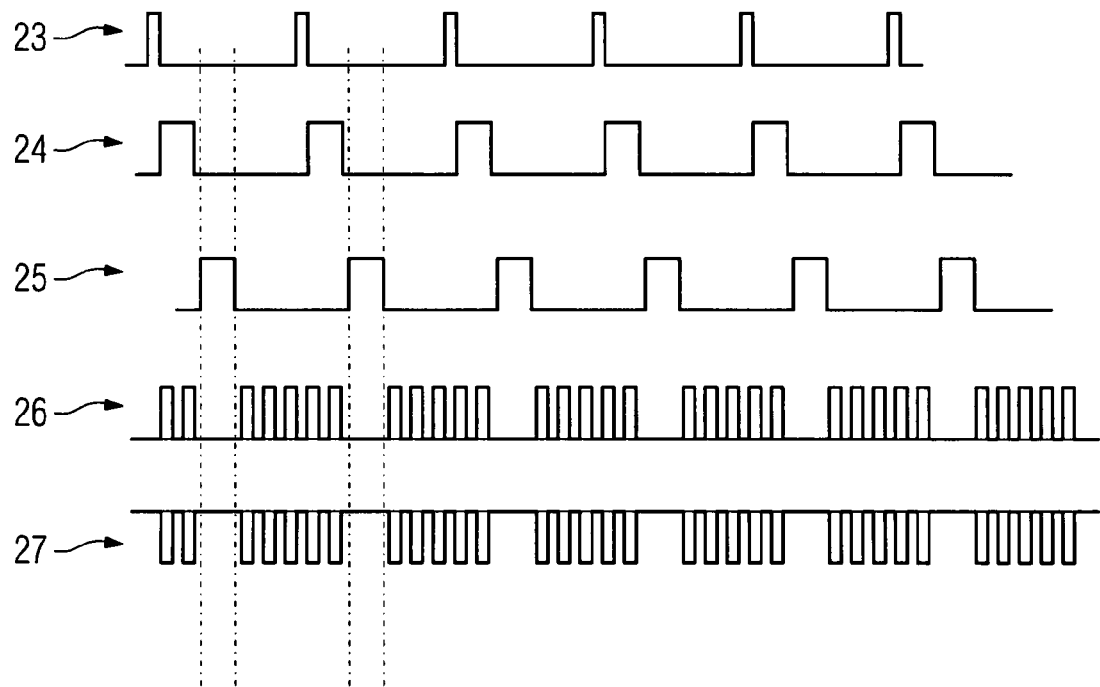
FIGS. 9 and 10 show a schematic representation of the synchronized current clock and image readout.
Figure 10:
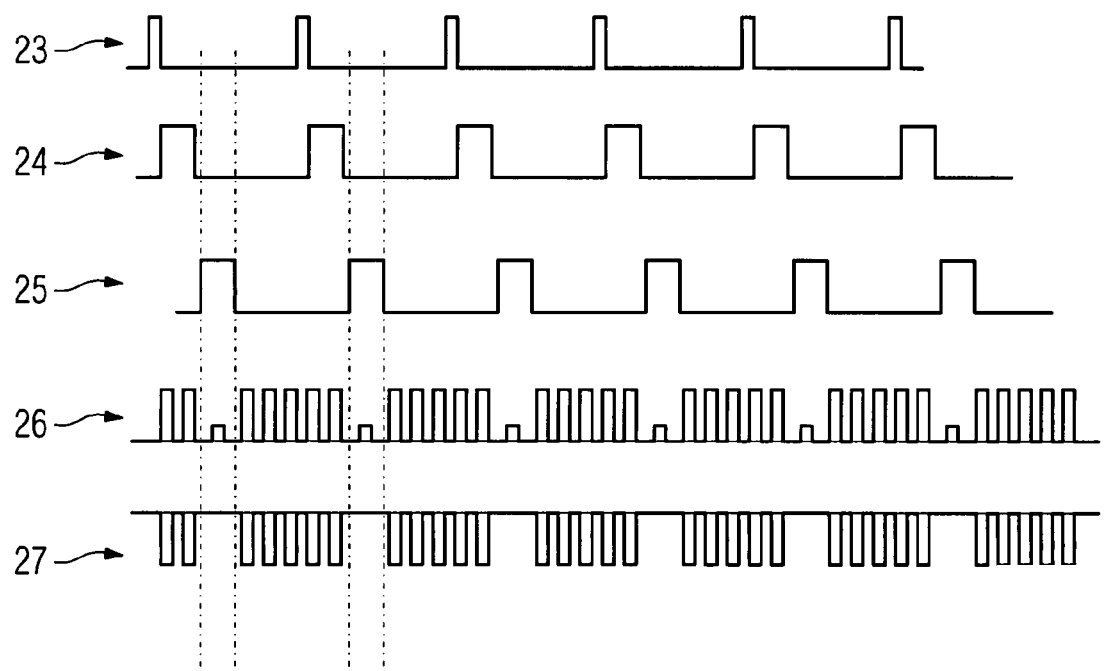

FIGS. 9 and 10 show the synchronized current clocking and image readout. The horizontal axis is in this case the time axis, the horizontal axis specifies from the bottom up the system clock 23, the x-rays 24 (in/out), the readout process 25 of the x-ray detector (in/out), the current clock 26 for the magnetic navigation (first coil) and the current clock 27 for the magnetic navigation (second coil). FIG. 9 shows that no or only a small amount of current for generating the electromagnetic navigation field is flowing when the x-ray detector is reading out, thereby preventing the occurrence of image artifacts. With the variant according to FIG. 10, only a minimal current for the magnetic navigation of the first coil flows, with the current being so minimal that it does not interfere with the readout of the x-ray detector and the image generation.

With other exemplary embodiments, there is a possibility of using more than one, preferably two robot systems. In this way, one robot system can be used to generate images and the other robot system can support the magnetic navigation coil. This is advantageous in that the magnetic navigation and the image generation can be implemented in parallel.

The invention claimed is:
1. A medical apparatus, comprising:
an electromagnet configured to generate a magnetic field to navigate a medical instrument, wherein the electromagnet is designed as a hollow cylinder, wherein the hollow cylinder is arranged on a bracket, wherein the bracket has a plurality of axes;
an x-ray device having an x-ray source and an x-ray detector, wherein the x-ray source and the x-ray detector are arranged on the electromagnet;
two ring coils parallel to one another and located at front ends of the hollow cylinder; and
a plurality of saddle coils between the ring coils arranged in a peripheral direction.

2. The medical apparatus as claimed in claim 1, wherein the medical apparatus is an examination apparatus, a treatment apparatus or a combination thereof.

3. The medical apparatus as claimed in claim 1, wherein the x-ray device supplies a visual control during the navigation.

4. The medical apparatus as claimed in claim 1, wherein the bracket has a plurality of mounting arm segments connected to one another.

5. The medical apparatus as claimed in claim 1, wherein the bracket is a multi-axis articulated aim robot.

6. The medical apparatus as claimed in claim 1, wherein the x-ray source and the x-ray detector are moveable along the periphery of the hollow cylinder by a drive.

7. The medical apparatus as claimed in claim 1, further comprising a control unit for moving the hollow cylinder.

8. The medical apparatus as claimed in claim 7, wherein the control unit controls a movement of the x-ray source and controls a movement of the x-ray detector.

9. The medical apparatus as claimed in claim 1, further comprising a cooling apparatus for at least one device selected from the group consisting of: the hollow cylinder, the x-ray source and the x-ray detector.

10. The medical apparatus as claimed in claim 1, wherein a control device controls the electromagnet.

11. The medical apparatus as claimed in claim 10, wherein a navigating of the medical instrument is based on influencing a current in the coil, wherein the coil is selcted from the group consisting of: the ring coil, the saddle coil and a combination thereof.

12. The medical apparatus as claimed in claim 11, wherein strength of the current or the current direction in the coil is changed based on the control device.

13. The medical apparatus as claimed in claim 1, wherein the saddle coils are rotateable relative to the ring coils about a longitudinal axis of the hollow cylinder.

14. The medical apparatus as claimed in claim 1, wherein the hollow cylinder has four saddle coils.

15. The medical apparatus as claimed in claim 1, further comprising a moveable patient support table, wherein the moveable patient support table is adjustable by a control, and wherein the adjustment of the moveable patient support table is synchronised with an adjustment of the hollow cylinder.

16. The medical apparatus as claimed in claim 1, wherein the x-ray detector has a shielding against magnetic fields.

17. The medical apparatus as claimed in claim 16, wherein the shielding comprises conductive nanoparticles.

18. The medical apparatus as claimed in claim 1, wherein a current clocking for generating the electromagnetic field for the navigation is synchronized with a readout of the x-ray detector.

19. A medical apparatus, comprising:
an electromagnet configured to generate a magnetic field to navigate a medical instrument, wherein the electromagnet is designed as a hollow cylinder, wherein the electromagnet is arranged on a second movable bracket with a second robot;
an x-ray device having an x-ray source and an x-ray detector, wherein the x-ray source and the x-ray detector are arranged on a first movable bracket with a first robot;
two ring coils parallel to one another and located at front ends of the hollow cylinder; and
a plurality of saddle coils between the ring coils arranged in a peripheral direction.

* * * * *